United States Patent
Li et al.

(10) Patent No.: US 10,953,062 B2
(45) Date of Patent: Mar. 23, 2021

(54) ANTICANCER PHARMACEUTICAL COMPOSITION AND APPLICATION THEREOF

(71) Applicant: GUIZHOU JIN QIAN FRUIT BIOTECHNOLOGY CO., LTD., Bijie (CN)

(72) Inventors: Shouqian Li, Bijie (CN); Shouyue Li, Bijie (CN); Yu Zhou, Bijie (CN)

(73) Assignee: GUIZHOU JIN QIAN FRUIT BIOTECHNOLOGY CO., LTD., Bijie (CN)

( * ) Notice: Subject to any disclaimer, the term of this patent is extended or adjusted under 35 U.S.C. 154(b) by 0 days.

(21) Appl. No.: 16/496,741

(22) PCT Filed: Mar. 22, 2018

(86) PCT No.: PCT/CN2018/080029
§ 371 (c)(1),
(2) Date: Sep. 23, 2019

(87) PCT Pub. No.: WO2018/171672
PCT Pub. Date: Sep. 27, 2018

(65) Prior Publication Data
US 2020/0030401 A1 Jan. 30, 2020

(30) Foreign Application Priority Data
Mar. 24, 2017 (CN) .......................... 201710184824.2

(51) Int. Cl.
| | | |
|---|---|---|
| *A61K 36/738* | (2006.01) |
| *A61P 35/00* | (2006.01) |
| *A61K 9/00* | (2006.01) |
| *A61K 36/074* | (2006.01) |
| *A61K 36/185* | (2006.01) |
| *A61K 36/38* | (2006.01) |
| *A61K 36/52* | (2006.01) |
| *A61K 36/71* | (2006.01) |
| *A61K 36/752* | (2006.01) |
| *A61K 36/889* | (2006.01) |
| *A61K 36/8988* | (2006.01) |

(52) U.S. Cl.
CPC .......... *A61K 36/738* (2013.01); *A61K 9/0053* (2013.01); *A61K 36/074* (2013.01); *A61K 36/185* (2013.01); *A61K 36/38* (2013.01); *A61K 36/52* (2013.01); *A61K 36/71* (2013.01); *A61K 36/752* (2013.01); *A61K 36/889* (2013.01); *A61K 36/8988* (2013.01); *A61P 35/00* (2018.01)

(58) Field of Classification Search
None
See application file for complete search history.

(56) References Cited

FOREIGN PATENT DOCUMENTS

| | | |
|---|---|---|
| CN | 1562129 A | 1/2005 |
| CN | 101023772 A | 8/2007 |
| CN | 102920892 A | 2/2013 |
| CN | 107126509 A | 9/2017 |

*Primary Examiner* — Susan Hoffman
(74) *Attorney, Agent, or Firm* — Troutman Pepper Hamilton Sanders LLP; Christopher C. Close, Jr.

(57) ABSTRACT

The present invention discloses an anticancer pharmaceutical composition, comprising the following materials in parts by weight: 0.5-30 parts of fruits/leaves of *Rosa roxburghii*, 0.5-30 parts of fruits/leaves of *Phyllanthus emblica*, 0.5-30 parts of peel/seeds of *Punica granatum*, 0.5-30 parts of honey, 0.5-30 parts of flesh/pericarp of *Garcinia mangostana*, 0.5-30 parts of coconuts, 0.5-30 parts of pulp/peel of *Citrus limon*, 0.5-30 parts of raw walnuts, 0.1-5 parts of *Rhizoma gastrodiae*, 0.1-5 parts of *Lucid ganoderma*, 0.1-5 parts of seeds/leaves of *Moringa oleifera*, 0.01-2 parts of *Radix ranunculi ternati* and 0.01-2 parts of *Rhizoma paridis*.

4 Claims, 2 Drawing Sheets

ANTICANCER PHARMACEUTICAL COMPOSITION AND APPLICATION THEREOF

TECHNICAL FIELD

The present invention belongs to the technical field of pharmaceuticals, and specifically relates to an anticancer pharmaceutical composition and an application thereof, and the composition is a broad-spectrum anticancer agent, and can be used in the treatment or adjunctive treatment of various cancers.

BACKGROUND

Cancer is a general term of a broad class of malignant tumors, and is one of the major diseases to threaten human health and life seriously. Cancer is mainly characterized in that cancer cells make endless proliferation and migration to constantly consume a lot of nutrients in patient's body and to release various toxins, resulting in emaciation, weakness, anemia, anorexia, fever, severe damage of organ functions, etc. Currently, there are two major therapeutic methods to treat malignant tumors, namely, western medicine treatment and Chinese traditional treatment; the western medicine treatment mainly includes operative treatment, radiotherapy, chemotherapy as well as immature targeted drug delivery and cell therapy, etc., usually, the method is mainly dominated by palliatives, which causes great damage and irreversible injuries to normal tissues of human body, resulting in great pain, e.g., dizziness, emesis, hair loss, organ failure, weakened immunity, etc. moreover, it is unaffordable for ordinary families.

Based on traditional Chinese medicine, the emergence and development of cancer is a combined action of extremely various complex internal and external factors, causing weak Qi and cancer toxin. Weak Qi is a pathological basis of cancer, and cancer toxin is a major pathogenic factor of cancer, therefore, to tonify Qi is a fundamental to treat cancer and to relieve cancer toxin is a key to treating cancer based on the theory of traditional Chinese medicine. In recent years, there are more and more studies and reports on the treatment of tumors by means of traditional Chinese medicine, and as a treatment means of cancer, the traditional Chinese medicine has been concerned by more and more people, but there are a few of anticancer pharmaceutical compositions capable of really enhancing immunity, delaying cell senescence, regulating internal circulation and expelling vivotoxins in the treatment of cancer and achieving significant therapeutic effect.

Therefore, to relieve cancer patients' pain and overcome a series of problems caused by conventional radiotherapy/chemotherapy, based on the understanding and analysis on the traditional Chinese medicine to pathogenesis of chronic inflammation, cyst and cancer, the inventor proposes an innovative therapeutic route, which diminishes inflammation and enables our body to recover normal immunity by enhancing immunity, regulating internal circulation, delaying cell senescence, and expelling vivotoxins and retained water, thus enabling human body recovering normal physiological status and achieving the purpose of cancer treatment. Over more than a decade of clinical practices and exploration, the inventor has optimized and adjusted the formula repeatedly to obtain the pharmaceutical composition of the present invention finally, and achieved unexpected anticancer effect.

SUMMARY

A technical problem to be solved by the present invention is to provide a composition with prevention and treatment of cancer, and the composition is a broad-spectrum anticancer agent.

Another technical problem to be solved by the present invention is to propose an application of the composition in cancer prevention and treatment and other related fields.

The specific technical solution of the present invention is as follows:

The present invention provides a composition, where the ingredients thereof include the following materials in parts by weight: 0.5-30 parts of fruits/leaves of *Rosa roxburghii*, 0.5-30 parts of fruits/leaves of *Phyllanthus emblica*, 0.5-30 parts of peel/seeds of *Punica granatum*, 0.5-30 parts of honey, 0.5-30 parts of flesh/pericarp of *Garcinia mangostana*, 0.5-30 parts of coconuts, 0.5-30 parts of pulp/peel of *Citrus limon*, 0.5-30 parts of raw walnuts, 0.1-5 parts of *Rhizoma gastrodiae*, 0.1-5 parts of *Lucid ganoderma*, 0.1-5 parts of seeds/leaves of *Moringa oleifera*, 0.01-2 parts of *Radix ranunculi ternati* and 0.01-2 parts of *Rhizoma paridis*.

Preferably, the ingredients according to the composition include the following parts by weight of materials: 1-20 parts of fruits/leaves of *Rosa roxburghii*, 1-20 parts of fruits/leaves of *Phyllanthus emblica*, 1-20 parts of peel/seeds of *Punica granatum*, 1-20 parts of honey, 1-20 parts of flesh/pericarp of *Garcinia mangostana*, 1-20 parts of coconuts, 1-20 parts of pulp/peel of *Citrus limon*, 1-20 parts of raw walnuts, 0.2-2 parts of *Rhizoma gastrodiae*, 0.2-2 parts of *Lucid ganoderma*, 0.2-2 parts of seeds/leaves of *Moringa oleifera*, 0.01-1 part of *Radix ranunculi ternati* and 0.01-1 part of *Rhizoma paridis*.

The present invention provides application parts and processing methods of materials in the above composition, where the fruits/leaves of *Rosa roxburghii* include fresh or dried *Rosa roxburghii* fruits and/or leaves; the fruits/leaves of *Phyllanthus emblica* include fresh or dried *Phyllanthus emblica* fruits and/or leaves; the peel/seeds of *Punica granatum* include fresh or dried *Punica granatum* peel and/or seeds; the flesh/pericarp of *Garcinia mangostana* includes fresh or dried *Garcinia mangostana* flesh and/or pericarp; the pulp/peel of *Citrus limon* includes fresh or dried *Citrus limon* pulp and/or peel; the seeds/leaves of *Moringa oleifera* include fresh or dried *Moringa oleifera* seeds and/or leaves.

The present invention provides a preparation method and dosage forms of the composition, where a preparation method of the composition is as follows: powder, solution or extract is prepared by one or more of the methods of crushing, decocting, alcohol-extracting, soaking, percolating and fermenting the materials, then prepared into oral dosage forms by conventional preparation means.

Preferably, the dosage forms of the composition of the present invention are tablets, granules, capsules, oral liquid, syrups, pills, ointments, liniments, etc.

The present invention provides an application of the composition, namely: an application in the preparation of drugs for treating cancer, drugs, health food and food for adjunctively treating cancer.

In the formula, the efficacy of each ingredient is as follows:

*Rosa roxburghii*: it is recorded in *A Supplement to the Compendium of Materia Medica* that *Rosa roxburghii* has the efficacy of promoting digestion and tonifying spleen, astringing to arrest diarrhea and relieving summer-heat, and modern studies indicate that *Rosa roxburghii* has the efficacy of regulating body immunity, delaying aging, detoxifying, resisting atherosclerosis and tumor, etc. in addition to application in the treatment of retention of food, abdominal distension, dysentery, enteritis, hypertension, vascular rupture hemorrhage, vitamin C deficiency and other diseases.

*Phyllanthus emblica*: tastes sweet, sour, astringent and cool, classified into meridian tropism of lung and stomach, and has the efficacy of removing pathogenic heat from blood, promoting digestion and invigorating stomach, promoting the secretion of saliva and relieving a cough, mainly used for treating blood-heat/blood stasis, dyspepsia, abdominal distension, cough, sore throat and thirst.

*Punica granatum*: tastes sour, astringent and mild, classified into meridian tropism of large intestine, lung and kidney, and has the efficacy of relieving diarrhea with astringents, hemostasis and expelling parasite.

Honey: tastes sweet, mild, classified into meridian tropism of lung, spleen and large intestine, and has the efficacy of strengthen the middle warmer, moistening dryness, relieving pain, detoxifying, used for treating stomach/abdomen pain, lung dryness and dry cough, intestinal dryness with constipation, and detoxifying monkshood agents.

*Garcinia mangostana*: used in the treatment of stomachache, diarrhea, dysentery, infected wound, suppuration, chronic ulcer, gonorrhoea and other diseases.

Coconut: tastes sweet and mild, classified into meridian tropism of stomach, spleen and large intestine, and has the efficacy of tonifying deficiency, tonifying Qi and dispelling the wind, eliminating malntrition and killing parasite; long-term administration may tonify Qi and make people enjoy smooth and rosy cheeks, tolerating hunger.

*Citrus limon*: has the efficacy of promoting the secretion of saliva, quenching thirst, clearing away summer heat, dredging stagnation, invigorating stomach, relieving pain, treating stasis, stomachache and loss of appetite.

Walnut: tastes sweet and warm, classified into meridian tropism of kidney, lung and large intestine, and has the efficacy of tonifying kidney, warming lung and lubricating intestine, and can be used in the treatment of kidney-yang insufficiency, soreness and weakness of waist and knees, impotence and spermatorrhea, deficiency-cold, cough and asthma, intestinal dryness with constipation.

*Rhizoma gastrodiae*: tastes sweet and mild, classified into meridian tropism of liver, and has the efficacy of expelling wind and spasmolysis, stabilizing the liver-yang, dredging collaterals, and can be used in the treatment of febrile convulsion, epileptic convulsion, tetanus, headache dizziness, paralysis and numbness of limbs, rheumatism.

*Lucid ganoderma*: tastes sweet and mild, classified into meridian tropism of heart, lung, liver and kidney, and has the efficacy of tonifying Qi and calming nerves, relieving cough and asthma, and can be used in the treatment of insomnia and palpitation, lung deficiency, cough and asthma, consumptive disease and shortness of breath, anorexia.

*Moringa oleifera* seeds: it has the efficacy of lowering the blood sugar, improving sleep, clearing intestinal tract and boosting metabolism, and it has the significant curative effect in toxin elimination, metabolism acceleration, decrease of blood lipids and blood pressure, weight loss, regulation of intestines and stomach, liver protection, abstinence, enhancement of immunity.

*Radix ranunculi ternati*: tastes sweet, pungent and warm, classified into meridian tropism of liver and lung, and has the efficacy of dissipating phlegm and resolving masses, removing toxicity for detumescence, and can be used in the treatment of scrofula and subcutaneous nodule, furunculosis and pyogenic infections, bite of snakeworm.

*Rhizoma paridis*: tastes bitter, slightly cold and mild toxicity, classified into meridian tropism of liver, and has the efficacy of clearing heat and removing toxicity, relieve swelling and pain, clearing away the liver-fire and arresting convulsion, and can be used in the treatment of furunculosis and carbuncle, swollen sore throat, bite of snakeworm, tumbling hurt and injury, infantile convulsion.

The formula is obtained by clinical practices and optimization for many years under the guidance of basic theory of traditional Chinese medicine. During formulation process, considering the heavy burden of heart, liver and kidney caused by poor health and low immunity of cancer patients, poor gastrointestinal function due to long-term bedridden state as well as cancer cells spread, long-term medication and other reasons, *Rosa roxburghii, Phyllanthus emblica, Punica granatum, Garcinia mangostana*, coconut, *Citrus limon, Moringa oleifera* seeds and other various antioxidant ingredients or medicinal materials for food and medicine which are capable of regulating gastroenteric function, increasing immunnity and resisting cell senescence are selected as a basic formula, the formula may supplement rich minerals, vitamins, SOD, amino acids and other nutrients required by our body while improving the gastroenteric function of cancer patients, eliminating vivotoxins and retained water, enhance internal circulation of the body, boost immunity and oxidation resistance without increasing the burden of visceral organs, thus eliminating inflammation and recovering normal immunity of our body, etc. Most of the cancer patients are weak and suffer hypofunction of visceral organs clinically, therefore, walnut, *Rhizoma gastrodiae* and *Rhizoma gastrodiae* are added in the formula, the walnut is classified into meridian tropism of kidney, lung and large intestine, and has the efficacy of tonifying the kidney, warming the lung and lubricating the intestine; *Rhizoma gastrodiae* is classified into meridian tropism of liver, and has the efficacy of dispelling the wind and stopping spasm, stabilizing liver Yang and dredging collaterals; *Lucid ganoderma* is classified into meridian tropism of heart, lung, liver and kidney, and has the efficacy of tonifying Qi and calming the nerves, relieving cough and asthma; these three medicinal materials may regulate and recover the function of major organs, thus further promoting the recovery of normal internal circulation of the body and the rebuilding of immunity. In the formula, *Radix ranunculi ternati* and *Rhizoma paridis* may eliminate the stubborn carbuncle and node of tumor sites of cancer patients, and disintegrate tumor toxin, thus enhancing the formula's efficacy of eliminating inflammation and vivotoxin, supplementing and enhancing the therapeutic effect of the formula. In the formula, honey may strengthen the middle warmer, moisten dryness, relieve pain and detoxify, moreover, it has the function of achieving compatibility of drugs efficacy and modifying the taste, capable of greatly improving the flavor of the formula and enhancing the compliance of patients. To sum up, the formula is reasonable and its major ingredients are coordinated and supplemented with each other to achieve medical compatibility, meanwhile, the formula has stronger effect of enhancing immunity, regulating internal circulation, delaying cell senescence, expelling vivotoxin and retained water, bringing better therapeutic effect to cancer patients.

The beneficial effects of the present invention are:

1) The composition of the present invention has significant therapeutic effect in the treatment of cancer; the composition may greatly relieve patients' pain in the adjuvant treatment of cancer chemotherapy, thus improving quality of life.

2) The composition provided by the present invention may enhance immunity, help improve internal circulation and expelling cancer toxin; and its instruction based upon basic theory of traditional Chinese medicine brings significant curative effect to various cancers, therefore, the composition has wide clinical uses.

3) Raw materials of the composition provided by the present invention are all from pure-natural Chinese herbal medicine or food, therefore, the composition is safe in application and has no toxic and side effects; the composition has wide and cheap raw materials, capable of greatly relieving patients' economical burden.

4) The composition of the present invention has simple preparation process, easy to use.

5) The composition of the present invention is obtained by repeated verification and optimization of clinical practices for many years based upon a scientific formula under the guidance of basic theory of traditional Chinese medicine; the formula achieves unexpected effect in cell assay, animal test and clinical application, and has outstanding advantages and higher application value, moreover, compared with a random composition of common anticancer Chinese herbal medicines, the composition has far better effect in the treatment of various cancers.

DETAILED DESCRIPTION

Figure 1:
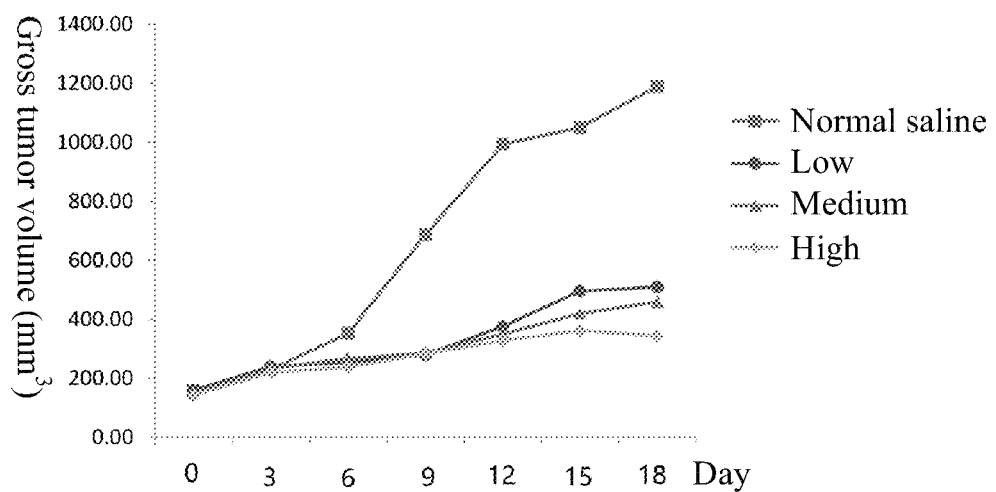
FIG. 1 is a diagram showing the change of gross tumor volume of a colorectal cancer HCT-116 over time (n=5).

The present invention will be described more specifically with reference to embodiments. It should be appreciated that implementation of the present invention is not limited to the embodiments below, and various changes and/or modifications made to the present invention in any form will fall within the scope of the present invention.

In the present invention, all parts and percentages are a unit of weight unless otherwise specified. Methods in the following embodiments are conventional methods of the field unless otherwise specified.

Embodiment 1

30 g fruits/leaves of *Rosa roxburghii*, 30 g fruits/leaves of *Phyllanthus emblica*, 30 g peel/seeds of *Punica granatum*, 18 g honey, 18 g flesh/pericarp of *Garcinia mangostana*, 18 g coconuts, 18 g pulp/peel of *Citrus limon*, 18 g raw walnuts, 5 g *Rhizoma gastrodiae*, 5 g *Lucid ganoderma*, 3 g seeds/leaves of *Moringa oleifera*, 2 g *Radix ranunculi ternati* and 2 g *Rhizoma paridis* were taken and added to 6 times of water according to gross weight of the formula, soaked for half an hour, decocted for twice 2 h each time, filtered, then soup was blended and added 30 g honey for mixing well.

Embodiment 2

0.5 g *Rosa roxburghii* fruits, 0.5 g *Phyllanthus emblica* leaves, 0.5 g *Punica granatum* peel, 1.5 g *Garcinia mangostana* pulp, 1.5 g coconuts, 1.5 g *Citrus limon* pulp, 1 g raw walnut, 0.5 g *Rhizoma gastrodiae*, 0.5 g *Lucid ganoderma*, 0.1 g *Moringa oleifera* seeds, 0.01 g *Radix ranunculi ternati* and 0.01 g *Rhizoma paridis* were taken and pulverized into fine powder, moreover, it was taken with 3 g honey by water.

Embodiment 3

2 g *Rosa roxburghii* leaves, 2 g *Phyllanthus emblica* fruits, 1 g *Punica granatum* seed, 0.5 g *Garcinia mangostana* pericarp, 0.5 g coconuts, 0.5 g *Citrus limon* peel, 0.5 g raw walnuts, 0.1 g *Rhizoma gastrodiae*, 0.1 g *Lucid ganoderma*, 0.5 g *Moringa oleifera* leaves, 0.5 g *Radix ranunculi ternati* and 0.05 g *Rhizoma paridis* were taken and pulverized into coarse powder, moreover, it was brewed with 3 g honey by boiled water.

Embodiment 4

27 g fruits/leaves of *Rosa roxburghii*, 27 g fruits/leaves of *Phyllanthus emblica*, 27 g peel/seeds of *Punica granatum*, 27 g honey, 15 g flesh/pericarp of *Garcinia mangostana*, 15 g coconuts, 15 g pulp/peel of *Citrus limon*, 15 g raw walnuts, 3 g *Rhizoma gastrodiae*, 3 g *Lucid ganoderma*, 3 g seeds/leaves of *Moringa oleifera*, 2 g *Radix ranunculi ternati* and 1 g *Rhizoma paridis* were taken and added to 3 times of water according to gross weight of the formula, sealed and fermented for 3 months in a cool place, then filtered to obtain the composition.

Embodiment 5

10 g fruits/leaves of *Rosa roxburghii*, 10 g fruits/leaves of *Phyllanthus emblica*, 10 g peel/seeds of *Punica granatum*, 30 g flesh/pericarp of *Garcinia mangostana*, 30 g coconuts, 30 g pulp/peel of *Citrus limon*, 30 g raw walnuts, 1 g *Rhizoma gastrodiae*, 1 g *Lucid ganoderma*, 5 g seeds/leaves of *Moringa oleifera*, 0.5 g *Radix ranunculi ternati* and 0.3 g *Rhizoma paridis* were taken, pulverized into coarse powder, soaked by 50% ethanol and percolated by flow rate of 2 ml/min for extraction, then 3 times of extracting solution according to the weight of the formula was collected, and 10 g honey was added for mixing well.

Embodiment 6

9 g fruits/leaves of *Rosa roxburghii*, 9 g fruits/leaves of *Phyllanthus emblica*, 9 g peel/seeds of *Punica granatum*, 6 g flesh/pericarp of *Garcinia mangostana*, 6 g coconuts, 6 g pulp/peel of *Citrus limon*, 6 g raw walnuts, 1.5 g *Rhizoma gastrodiae*, 1.5 g *Lucid ganoderma*, 1.5 g seeds/leaves of *Moringa oleifera*, 0.6 g *Radix ranunculi ternati* and 0.3 g *Rhizoma paridis* were taken and added to 6 times of water according to gross weight of the formula, soaked for half an hour, extracted for twice 2 h each time, filtered, then soup was blended and concentrated to relative density=1.1-1.2 g/ml (60° C.) to obtain an extract, then 9 g honey and a proper amount of excipients were added to the extract for granulation and drying, finally subpackaged into granules or compressed into troches or filled into capsules.

Embodiment 7

25 kg fruits/leaves of *Rosa roxburghii*, 30 kg fruits/leaves of *Phyllanthus emblica*, 20 kg peel/seeds of *Punica granatum*, 18 kg flesh/pericarp of *Garcinia mangostana*, 10 kg coconuts, 10 kg pulp/peel of *Citrus limon*, 18 kg raw walnuts, 5 kg *Rhizoma gastrodiae*, 3 kg *Lucid ganoderma*, 3 kg seeds/leaves of *Moringa oleifera*, 2 kg *Radix ranunculi*

*ternati* and 1 kg *Rhizoma paridis* were taken and added to 6 times of water according to gross weight of the formula, soaked for half an hour, decocted for twice 2 h each time, filtered, then soup was blended and added 30 kg honey for mixing well, subpackaged into 100 ml/bottle.

Embodiment 8

30 kg fruits/leaves of *Rosa roxburghii*, 27 kg fruits/leaves of *Phyllanthus emblica*, 27 kg peel/seeds of *Punica granatum*, 25 kg flesh/pericarp of *Garcinia mangostana*, 15 g coconuts, 10 kg pulp/peel of *Citrus limon*, 15 kg raw walnuts, 6 kg *Rhizoma gastrodiae*, 3 kg *Lucid ganoderma*, 5 kg seeds/leaves of *Moringa oleifera*, 2 kg *Radix ranunculi ternati* and 2 kg *Rhizoma paridis* were taken and added to 3 times of water according to gross weight of the formula, sealed and fermented for 3 months in a cool place, filtered and subpackaged into 100 ml/bottle.

Embodiment 9

10 kg fruits/leaves of *Rosa roxburghii*, 8 kg fruits/leaves of *Phyllanthus emblica*, 10 kg peel/seeds of *Punica granatum*, 15 kg flesh/pericarp of *Garcinia mangostana*, 20 kg coconuts, 20 kg pulp/peel of *Citrus limon*, 10 kg raw walnuts, 1 kg *Rhizoma gastrodiae*, 1 kg *Lucid ganoderma*, 5 kg seeds/leaves of *Moringa oleifera*, 0.5 kg *Radix ranunculi ternati* and 0.6 kg *Rhizoma paridis* were taken, pulverized into coarse powder, soaked by 50% ethanol and percolated by flow rate of 30 ml/min for extraction, then 3 times of extracting solution according to the weight of the formula was collected, and 10 g honey was added for mixing well, then subpackaged into 100 ml/bottle.

Embodiment 10

9 kg fruits/leaves of *Rosa roxburghii*, 12 kg fruits/leaves of *Phyllanthus emblica*, 6 kg peel/seeds of *Punica granatum*, 9 kg flesh/pericarp of *Garcinia mangostana*, 6 kg coconuts, 15 kg pulp/peel of *Citrus limon*, 6 kg raw walnuts, 1 kg *Rhizoma gastrodiae*, 1.5 kg *Lucid ganoderma*, 1.5 kg seeds/leaves of *Moringa oleifera*, 1 kg *Radix ranunculi ternati* and 0.6 kg *Rhizoma paridis* were taken and added to 6 times of water according to gross weight of the formula, soaked for half an hour, extracted for twice 2 h each time, filtered, then soup was blended and concentrated to relative density=1.1-1.2 g/ml (60° C.) to obtain an extract, then 12 kg honey and a proper amount of excipients were added to the extract for granulation and drying, finally subpackaged into granules or compressed into troches or filled into capsules.

Embodiment 11 Research Results of In-Vitro Anticancer Activity of the Composition of the Present Invention To evaluate the in-vitro anticancer activity of the composition of the present invention, MTT was adopted by the inventor to research the growth inhibitory activity of samples in embodiment 8 in the composition of the present invention on 20 kinds of tumor cell strains, including lung cancer, colorectal cancer, breast cancer, esophagus cancer, leukaemia, liver cancer, prostatic cancer, cervical cancer, stomach cancer and osteosarcoma.

Medicine preparation: samples of Embodiment 8 was taken and filtered for sterilization by a 0.22 μm aqueous millipore filter, subpackaged and placed for further use at room temperature. Samples were taken out in use, and placed for 20 min at room temperature, shaken well and diluted by a medium to 12.5%, 6.25%, 3.125%, 1.5625%, 0.78125%, 0.390625%, 0.1953125%, 0.09765625%, 0.048828125% of the original concentration.

All cells were purchased from ATCC; serum: imported Gibco fetal calf serum; DMSO: Sigma; other all reagents and consumables were imported.

Cell experiment procedure: cells cryopreserved in a liquid nitrogen container (purchased from ATCC) were taken, dissolved into 37° C. a water bath and centrifuged for 3 min by 800 rmp to remove supernatant, added to corresponding media for culture, and media change was conducted in the next day, then cell subculture was implemented after reaching proper growth density; after cells were subcultured for twice to be in a good state and logarithmic growth, the cells were digested (media were discarded, 1 ml pancreatin was added for washing, then 1 ml pancreatin was added for digestion for about 4 min, and the digestion time is determined according to the cell, at the end of digestion, a 2 ml medium containing 10% serum and antibiotics was added for cell neutralization, then the cells were pipetted to a 50 ml BD tube and centrifuged for 3 min by 1000 rmp); supernatant of the centrifuged cells was removed, pipetted onto a 10 ml medium for dilution, after mixed well, partial cells were taken for subculture. Suspension was counted on a cell counting chamber and inoculated on a 96-hole plate with certain density, the side hole was filled by normal saline with 100 ul medium per hole, after cell adherence, certain concentration of medicine was added; after 72 h of culture, 20 ul MTT (5 mg/ml) was added per hole for action for 4 h, liquid was absorbed by a suction device, then 150 ul DMSO was added per hole for oscillation on a shaker for about 10 min, a microplate reader was used to test photometric values at 490 and 570; inhibition rate was calculated according to data absorbance, then median inhibitory concentration IC50 was calculated, and the results were shown in the table below specifically.

TABLE 1

| In-vitro antitumor activity (n = 3) | |
| --- | --- |
| Tumor cell | Diluted concentration after being up to $IC_{50}$ |
| A549 | (0.55 ± 0.07)% |
| H1299 | (0.48 ± 0.26)% |
| H1975 | (1.61 ± 0.33)% |
| HCT-116 | (1.26 ± 0.10)% |
| HT-29 | (6.27 ± 1.25)% |
| SW620 | (2.65 ± 1.30)% |
| K562 | (0.58 ± 0.19)% |
| MV4-11 | (1.21 ± 0.16)% |
| PC3 | (1.22 ± 0.33)% |
| DU145 | (0.85 ± 0.21)% |
| MCF7 | (1.15 ± 0.35)% |
| MDA-MB-453 | (1.59 ± 0.33)% |
| MDA-MB-231 | (2.21 ± 0.16)% |
| ECA-109 | (9.28 ± 1.73)% |
| KYSE-150 | (2.08 ± 0.57)% |
| BGC-823 | (6.98 ± 2.50)% |
| HepG2 | (3.12 ± 0.64)% |
| BELE-7404 | (3.95 ± 1.49)% |
| Hela | (1.7 ± 0.29)% |
| 143B | (2.54 ± 0.15)% |

It can be seen from table 1 that the sample in Embodiment 8 of the composition of the present invention has good growth inhibitory activity to the 20 tumor cell strains, showing that the drug has broad-spectrum antitumor activity. In the table, data with % shows that it is diluted to a certain percentage of the original concentration, and half of cancer cells will die at the concentration.

Embodiment 12 Research on In-Vitro Anticancer Activity of the Composition of the Present Invention To evaluate the in-vitro anticancer effect of the composition of the present invention, a sample of Embodiment 7 was adopted by the inventor to study the growth inhibition of the sample of Embodiment 7 in the composition of the present invention on three subcutaneous tumors of naked mice, namely, colorectal cancer cells HCT-116, breast cancer MDA-MB-231 and non-small cell lung cancer H1975.

Test Procedure

Animal feeding: Bulb/c naked mice (grade SPF, 17-18 g and 6-8 weeks) were taken (purchased from Beijing Vital River Laboratory Animal Technology Co., Ltd.) and raised in an SPF animal house with breeding fodder, 5 pieces per cage, padding, water and fodder were replaced per week, iron shelves and covers were replaced per month.

Cancer cell culture: cells HCT-116, MDA-MB-231 and H1975 were cultured, HCT-116 and MDA-MB-231 were cultured on a DMEM medium, H1975 was cultured on a 1640 medium, Shuangyou (containing antibiotics and 10% fetal calf serum), the cell-culture dish was WHB. When it was estimated that there were enough cells, cells were collected and removed from the media, then digested by a pancreatin, at the end of digestion, Shuangyou was added to terminate digestion; the collected cells were placed into a 50 ml BD tube and centrifuged for 3 min by 1000 rmp, then washed for 3 times by corresponding serum-free media and centrifuged for 3 min by 1000 rmp each time; cell counting was conducted by a counting plate, and cells were diluted to $1*10^8$/ml;

Tumor inoculation: the cultured tumor cells were brought into an animal house by a conserved tube, $1*10^7$ tumor cells were inoculated on fore limbs of each naked mouse on a super clean bench (it should be guaranteed that cells were mixed well before inoculation).

Grouping and administration: the growth situation of subcutaneous tumors was observed every day three days later, tumors were divided into groups according to volume (large, middle and small) when the gross volume was up to about 100 mm$^3$, there is a little difference of volume in each group of the tumor, 5 naked mice in each group; a normal saline group, high-dose drug group (0.8 ml, concentrated to a half of the original volume), medium-dose drug group (0.4 ml) and low-dose drug group (0.2 ml), the high-dose group is equivalent to a 300 ml dosage taken by people, and the gross tumor volume was recorded; administration was implemented every day, and volume of the tumor was measured every other 3 days.

Figure 2:
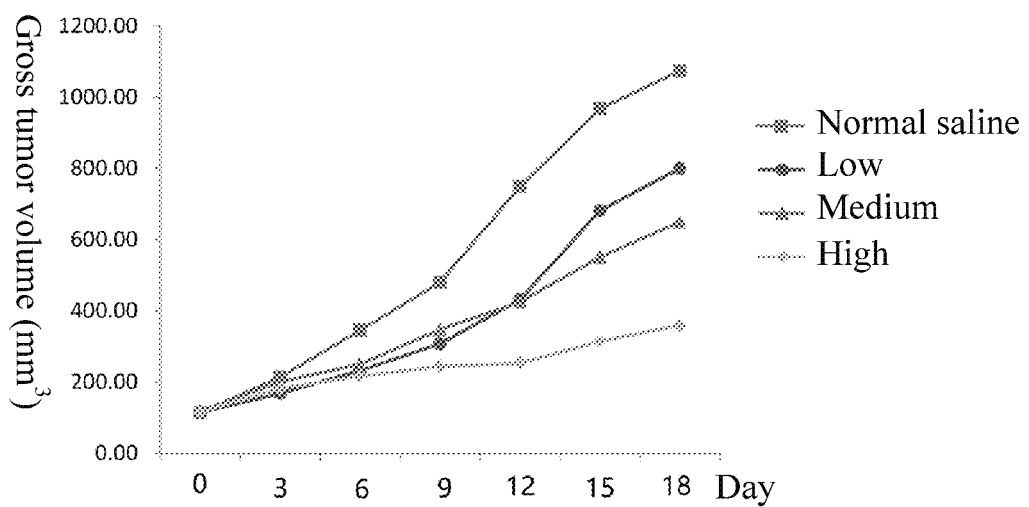
FIG. 2 is a diagram showing the change of gross tumor volume of a breast cancer MDA-MB-231 over time (n=5).
Figure 3:
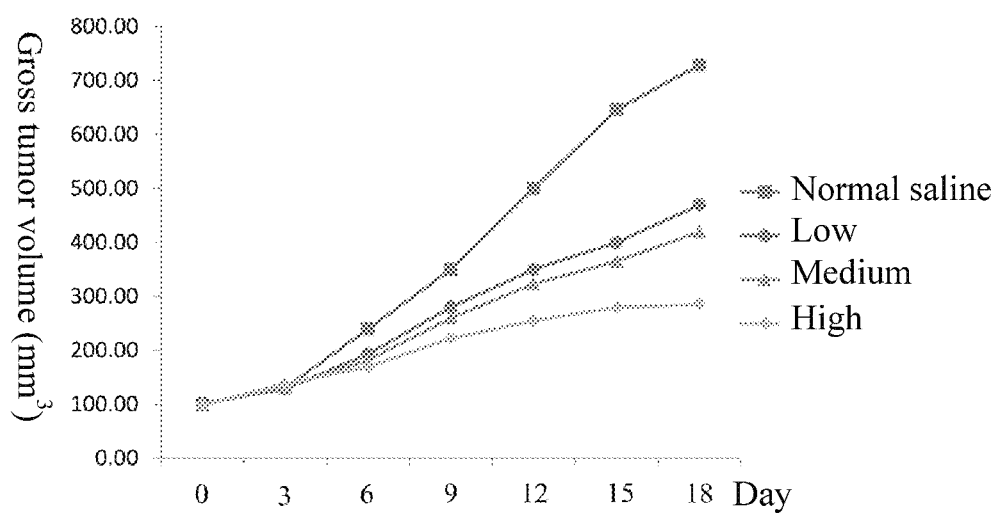
FIG. 3 is a diagram showing the change of gross tumor volume of a lung cancer H1975 over time (n=5).

Test results and data statistics: the data was collected after administration was implemented for 18 d, results indicate that: the composition of the present invention has prominent in-vivo inhibition effect to the three subcutaneous tumors, and the anti-tumor rate to the colorectal cancer HCT-116, breast cancer MDA-MB-231 and lung cancer H-1975 is respectively 71.1%, 66.5% and 60.9%, see details in FIG. 1, FIG. 2 and FIG. 3 of the description.

Supplementary instruction: the dosage of administration is 0.4 ml normal saline per day, the low-dose group is 0.4 ml of the normal saline diluted for one fold, the medial-dose group is 0.4 ml per day and the high-dosage group is 0.4 ml of the normal saline concentrated one fold.

Embodiment 13 Clinical Application Effect of the Composition of the Present Invention The composition of the present invention has been clinically applied for more than a decade, and by clinical verifications of hundreds of patients, the composition may significantly improve immunity, help improve internal circulation and expelling cancer toxin, and have good therapeutic effect, therefore, the composition has wide clinical uses. The composition may greatly relieve patients' pain in the adjuvant treatment of cancer chemotherapy, thus improving quality of life. The following are partial typical cases of the composition in clinical application:

1. Zeng XXX, female, 45 years old. The patient suffered a 32.5*16.4 mm lump in her right breast with prickling pain. The patient received a CT scanning after taking 300 ml drug in Embodiment 1 of the composition for 100 d, no abnormal density can be found partially.

2. Xu XXX, a male student, 18 years old. The patient was skin and bones, looked pale and suffered left paralysis, moreover definitely diagnosed advanced angioma (lesion was located outside the right thigh, volume was 51.8*13.0 mm) by examination, the hospital believed that there was a small chance of success (only 20%) by chemotherapy and suggested him to receive a amputation. After taking the sample of Embodiment 9 of the composition for three courses of treatment (21 d for a course of treatment, 3 times a day and 100 ml each time), the bump shrunk to 16.0*7.2 mm and changed to benign cyst; after the composition was continuously taken for a course of treatment, the lump disappeared, and the patient has basically recovered normal physiological function.

3. Peng XXX, male, 60 years old. The patient suffered a prostatic cancer with lung metastasis, after receiving chemotherapy for two courses of treatment, the patient failed to receive chemotherapy continuously due to organ failure caused by general weakness, hair loss, multiple small lymph nodes, therefore, the patient was suggested to recuperate at home for 2 months (actually suggested to give up the treatment). The patient has resumed normal activity and taken care of himself in daily life after taking the composition (the sample of Embodiment 5) for 3 times per day and 100 ml each time for two courses of treatment (60 d). By examination, prostate glands got normal in size and shape, the transparency of lungs increased, and no obvious node was found; the patient recovered normal basically after taking the composition for two courses of treatment continuously.

4. Dai XXX, male, 52 years old. CT results of the patient: 1) .S8, S5/6 space occupying lesion, inclined to malignant space occupying. 2). liver cirrhosis, splenectasis, large amount of ascitic fluid. 3). inflammatory lesions of lower lungs and bilateral seroperitoneum. 4). soft tissue swelling in bilateral paries ventralis. The patient suffered complete edema below chest, failed to eat and defecate, strictly was confined to bed, after injecting natriuretic injection, his all-day urine output was 350 ml only. The patient recovered 3000 ml urine output, made normal defecation and achieved detumescence three days later after taking the composition (the sample in Embodiment 4) for three times a day and 50 ml each time; after taking the composition for about two courses of treatment, the patient got elimination of body swelling, and can walk autonomously; after taking the composition for three courses of treatment continuously, the patient has recovered basically.

5. Xu XXX, female, 39 years old. By transvaginal ultrasonography, the uterine size of the patient was 72*64*74 mm, anteversion of uterus enlarged, echo of myometrial cells was nonuniform, multiple different sizes of echo masses, the largest one was located in rear wall and about 37*34 mm, and the internal echo was not homogenous, therefore, the patient was diagnosed with multiple myomata. After taking the composition of Embodiment 3 (the product was brewed as a tea drink to replace daily drinking), 100 days later, by transvaginal ultrasonography, her uterine veil was basically smooth and complete, echo was homogeneous, several echoless dark regions may be discovered at the cervix uteri, a larger one was about 4*3 mm.

What is claimed is:

1. An anticancer pharmaceutical composition, comprising the following materials in parts by weight: 0.5-30 parts of fruits and/or leaves of *Rosa roxburghii*, 0.5-30 parts of fruits and/or leaves of *Phyllanthus emblica*, 0.5-30 parts of peel and/or seeds of *Punica granatum*, 0.5-30 parts of honey, 0.5-30 parts of flesh and/or pericarp of *Garcinia mangostana*, 0.5-30 parts of coconuts, 0.5-30 parts of pulp and/or peel of *Citrus limon*, 0.5-30 parts of raw walnuts, 0.1-5 parts of *Rhizoma gastrodiae*, 0.1-5 parts of *Lucid ganoderma*, 0.1-5 parts of seeds and/or leaves of *Moringa oleifera*, 0.01-2 parts of *Radix ranunculi ternati* and 0.01-2 parts of *Rhizoma paridis*;

wherein the fruits and/or leaves of *Rosa roxburghii* is selected from any one of fresh *Rosa roxburghii* fruits, dried *Rosa roxburghii* fruits, fresh *Rosa roxburghii* leaves and dried *Rosa roxburghii* leaves, or any combination thereof; the fruits and/or leaves of *Phyllanthus emblica* is selected from any one of fresh *Phyllanthus emblica* fruits, dried *Phyllanthus emblica* fruits, fresh *Phyllanthus emblica* leaves and dried *Phyllanthus emblica* leaves, or any combination thereof; the peel and/or seeds of *Punica granatum* is selected from any one of fresh *Punica granatum* peel, dried *Punica granatum* peel, fresh *Punica granatum* seeds, and dried *Punica granatum* seeds, or any combination thereof; the flesh and/or pericarp of *Garcinia mangostana* is selected from any one of fresh *Garcinia mangostana* flesh, dried *Garcinia mangostana* flesh, fresh *Garcinia mangostana* pericarp and dried *Garcinia mangostana* pericarp, or any combination thereof; the pulp and/or peel of *Citrus limon* is selected from any one of fresh *Citrus limon* pulp, dried *Citrus limon* pulp, fresh *Citrus limon* peel and dried *Citrus limon* peel, or any combination thereof; and the seeds and/or leaves of *Moringa oleifera* is selected from any one of fresh *Moringa oleifera* seeds, dried *Moringa oleifera* seeds, fresh *Moringa oleifera* leaves and dried *Moringa oleifera* leaves, or any combination thereof; and wherein the dosage forms of the anticancer pharmaceutical composition are tablets, capsules, pills, ointments, or liniments.

2. The composition according to claim 1, comprising the following materials in parts by weight: 1-20 parts of fruits and/or leaves of *Rosa roxburghii*, 1-20 parts of fruits and/or leaves of *Phyllanthus emblica*, 1-20 parts of peel and/or seeds of *Punica granatum*, 1-20 parts of honey, 1-20 parts of flesh and/or pericarp of *Garcinia mangostana*, 1-20 parts of coconuts, 1-20 parts of pulp and/or peel of *Citrus limon*, 1-20 parts of raw walnuts, 0.2-2 parts of *Rhizoma gastrodiae*, 0.2-2 parts of *Lucid ganoderma*, 0.2-2 parts of seeds and/or leaves of *Moringa oleifera*, 0.01-1 part of *Radix ranunculi ternati* and 0.01-1 part of *Rhizoma paridis*.

3. A method for treating or adjunctively treating cancer, the method comprising administering (i) drugs, (ii) health food or (iii) food prepared from the anticancer pharmaceutical composition of claim 1.

4. A method for treating or adjunctively treating cancer, the method comprising administering (i) drugs, (ii) health food or (iii) food prepared from the anticancer pharmaceutical composition of claim 2.

* * * * *